(12) United States Patent
Han et al.

(10) Patent No.: US 11,415,649 B2
(45) Date of Patent: Aug. 16, 2022

(54) MAGNETIC RESONANCE COILS FOR SIMULTANEOUS IMAGING AND B0 SHIMMING

(71) Applicant: Cedars-Sinai Medical Center, Los Angeles, CA (US)

(72) Inventors: Hui Han, West Hollywood, CA (US); Debiao Li, South Pasadena, CA (US)

(*) Notice: Subject to any disclaimer, the term of this patent is extended or adjusted under 35 U.S.C. 154(b) by 20 days.

(21) Appl. No.: 16/650,227

(22) PCT Filed: Sep. 28, 2018

(86) PCT No.: PCT/US2018/053434
§ 371 (c)(1),
(2) Date: Mar. 24, 2020

(87) PCT Pub. No.: WO2019/067905
PCT Pub. Date: Apr. 4, 2019

(65) Prior Publication Data
US 2020/0271736 A1 Aug. 27, 2020

Related U.S. Application Data

(60) Provisional application No. 62/564,883, filed on Sep. 28, 2017.

(51) Int. Cl.
*G01R 33/3415* (2006.01)
*A61B 5/055* (2006.01)
(Continued)

(52) U.S. Cl.
CPC ......... *G01R 33/3415* (2013.01); *A61B 5/055* (2013.01); *G01R 33/34092* (2013.01);
(Continued)

(58) Field of Classification Search
CPC ......... G01R 33/34092; G01R 33/3415; G01R 33/3635; G01R 33/3808; G01R 33/3815;
(Continued)

(56) References Cited

U.S. PATENT DOCUMENTS 7,375,518 B2   5/2008  Kurome
7,622,928 B2  11/2009  Gauss
(Continued)

FOREIGN PATENT DOCUMENTS

WO   WO 2017/079487 A1   5/2017

OTHER PUBLICATIONS

Keil, B., "Construction of Receive Arrays," Proceedings for the International Society for Magnetic Resonance in Medicine 21, pp. 1-10 (2013).
(Continued)

*Primary Examiner* — Gregory H Curran

(57) ABSTRACT

A coil assembly for MR imaging includes an RF coil element and a shim coil array with a shim coil element. The shim coil element is physically separated from the RF coil element. The shim coil element includes a DC current loop having a DC power supply connection to allow DC current to generate a local B0 magnetic field. The coil assembly simultaneously provides an RF mode for at least one of transmit or receive and a direct current mode to generate a local B0 magnetic field for at least one of B0 shimming an imaging space, MRI spatial encoding of tissue spins, or MRI temporal encoding of tissue spins. The mutual inductance between the shim coil element and the RF coil element is minimized by configuration of blocking elements in the shim coil in order to minimize the RF interaction there between.

28 Claims, 8 Drawing Sheets

(51) Int. Cl.
    *G01R 33/34*         (2006.01)
    *G01R 33/36*         (2006.01)
    *G01R 33/38*         (2006.01)
    *G01R 33/3815*      (2006.01)
    *G01R 33/3875*      (2006.01)
    *G01R 33/48*         (2006.01)

(52) U.S. Cl.
    CPC ..... *G01R 33/3635* (2013.01); *G01R 33/3808* (2013.01); *G01R 33/3815* (2013.01); *G01R 33/3875* (2013.01); *G01R 33/4806* (2013.01)

(58) Field of Classification Search
    CPC .. G01R 33/3875; G01R 33/4806; A61B 5/055
    See application file for complete search history.

(56) References Cited

U.S. PATENT DOCUMENTS

| | | | |
|---|---|---|---|
| 9,891,299 B1* | 2/2018 | Stormont | G01R 33/3873 |
| 2016/0116556 A1* | 4/2016 | Darnell | G01R 33/3875 324/307 |

OTHER PUBLICATIONS

International Search Report and Written Opinion in International Application No. PCT/US2018/053434, dated Dec. 4, 2018 (12 pages).

* cited by examiner

MAGNETIC RESONANCE COILS FOR SIMULTANEOUS IMAGING AND B0 SHIMMING

CROSS-REFERENCE TO RELATED APPLICATIONS

This application is a U.S. national stage of International Application No. PCT/US2018/053434, filed Sep. 28, 2018, which claims priority to and the benefit of U.S. Provisional Patent Application No. 62/564,883, filed Sep. 28, 2017, each of which is hereby incorporated by reference herein in its entirety.

TECHNICAL FIELD

The present disclosure relates to systems and methods for magnetic resonance imaging. More specifically, the present disclosure relates to a unified coil (UNIC) system consisting of separate RF and shim coil arrays

BACKGROUND

During the past few decades, major developments in magnetic resonance imaging (MRI) scanner technology have been driven by the ever-increasing demand for higher static magnetic field (B0) strengths, prevalently 1.5 Tesla a decade ago, now 3 Tesla, and in the future probably 7 Tesla. As is understood, MRI uses such powerful magnets to generate a magnetic field over the area of scanning interest. An MRI scanner uses a radio frequency (RF) coil or coil array that generates radio frequency (RF) waves into the area of interest. A transmitting RF coil is used to generate the RF magnetic field and a receiver RF coil is used to receive RF signals from the area of interest that indicate the composition of the tissue. The static magnetic field (B0) inhomogeneity has always been one major challenge with increased field strengths. Another major challenge is the inhomogeneity of the radio frequency (RF) magnetic field (B1). Many off-resonance imaging problems are essentially attributed to B0 field inhomogeneities, which are unfortunately proportional to the B0 field strength. For example, image artifacts and signal voids compromise whole brain functional imaging particularly in prefrontal cortex and temporal cortex and cardiac SSFP imaging particularly at 3 Tesla and higher field strengths. The shimming magnetic field is used to adjust the homogeneity of the static magnetic field (B0) and therefore remedy the inhomogeneity of the static magnetic field (B0).

The RF coils in current scanner designs are placed in proximity to the area of interest. For example, the magnet to generate the static magnetic field may be located in a tube around a patient, while the RF coil is located nearer to the chest of the patient in the tube. A shim coil can be placed in the tube to produce the shimming magnetic field. However, there are competing concerns with the placement of the RF coil and the shimming coil. The RF coil must be placed close enough to the target object to actually obtain imaging data of the target object with a maximized RF sensitivity or signal-to-noise ratio (SNR). Similarly, the shim coil must generally be placed close enough to actual provide more effective local shimming to the static localized B0 inhomogenous magnetic field. However, placing the shim coil too close to the RF coil will lead to a loss of RF sensitivity in the RF coil due to the mutual inductance between the RF coil and the shim coil, which leads to a reduction in the signal-to-noise ration of the RF signal received from the target object. Thus, placing shim coil array outside the RF coil array or inside the RF coil array may present certain problems, including a decrease in shimming performance and/or a loss of RF sensitivity leading to a damping in RF sensitivity of the received signals. The RF coil (either an RF-receive coil or a dual RF-transmit/receive coil) can be shielded from an interior shim coil, but generally this presents difficulties in transmitting the RF signal to the target object, which is not desirable for modern MRI scanners.

Since 2012, a new platform MR coil technology, known as an "iPRES" coil, has been proposed to solve the challenge of the inhomogeneities of the static magnetic field (B0). "iPRES" is defined as integrated, parallel, reception, excitation, and shimming. The iPRES coil system is an integrated RF and B0 shimming coil array. Such a system is described in U.S. Patent Publication No. 2014/0002084 to inventors Hui Han, Trong-Kha Truong, and Allen Song at the Duke University Medical Center.

The iPRES concept uses a single coil array rather than separate coil arrays for parallel RF reception/transmission and B0 field shimming. It relies on a circuit design that allows a radio frequency current for excitation/reception and a direct current for B0 shimming to coexist independently in the same physical coil loop or conductor. The underlying principle that currents or waves at different frequencies can coexist independently in the same conductor or media without undesired interference between them is simple and widespread in the electro-physics and communications fields.

The iPRES system has now been regarded as probably the most efficient and easy to implement shimming technology compared to all other existing shimming techniques including in-scanner spherical harmonic (SH) shim coils, multi-coil shimming techniques using separate shim coils/elements distantly located from an RF coil array. The localized multi-coil shimming functionality inherently provided by the same RF/DC coil loops can address many off-resonance imaging problems due to air/Bone/tissue susceptibility differences in brain, cardiac, and musculoskeletal imaging at an unprecedented level, thus greatly increasing image fidelity and resolution in problematic regions of interest. The iPRES technology may be applied to a range of coils from head coils, cardiac coils, musculoskeletal coils, breast coils, knee coils, and etc. Such integrated RF/shim arrays will likely replace current generation RF coil array with minimal modification of MRI system hardware architecture.

Although largely surpassing other existing technologies, there are still two critical limitations inherent in iPRES coils, particularly for 3T & 1.5T human body MRI scanners, prevalent in most hospitals and research institutes, and all animal MRI scanners. First, the size, shape, and position of the DC shim loops are limited to the same as the RF loops because Both RF and DC currents flow in the same conductor/loop. Second, the number of DC shim coil loops for an iPRES coil is limited by the number of available RF receivers, i.e., 32 RF receivers (with 32 shim coils) in state-of-the-art 3T human body scanners and 16 or 8 RF receivers (with 16 or 8 shim coils) in many 1.5T/3T scanners, and 1-8 RF receivers (with 1-8 shim coils) in most animal scanners.

These limitations largely constrain the effectiveness of shimming that prevents increasing the number of shim coils. Increasing the number of shim coils (i.e., the number of freedoms) can dramatically improve shimming effectiveness. Equally important, the size of the shim coils should match the dimension of anatomical structures possessing high-order (above second order) field inhomogeneities due to air/Bone/tissue susceptibility differences, in order to generate opposite high-order shim fields to cancel the inhomogeneous field within those anatomical structures.

More recently, a coil design concept has been proposed in which integrated RF and B0 shimming is provided which applicable to almost all MRI coils and systems. This coil design involves using physically separate RF and shim coil in combination with geometrical decoupling methods to minimize the distance between separate shim and RF loops and enable shim loops to physically free from the RF loops. This is described in International Patent Publication No. WO 2017/079847 to inventors Hui Han and Debaio Li. Therefore, Both RF and shim coils can be in dose proximity to the subject and be designed independently to maximize the performance of each function. However, while such a coil design concept is advantageous in several respects, the need to design the RF and shim loops to provide the necessary geometrical decoupling increases the complexity of the design.

Thus, there is a need for a magnetic resonance coil system that allows for more shim coils than the number of RF receiver channels to improve shimming effectiveness. There is also a need for a coil system that allows separate RF and shim loop arrays that overlap and share the same surface or layer of a coil mechanical supporting structure with a minimal distance between them to improve shimming effectiveness. There is also a need for a coil system that does not require the increase of the radial diameter of a MRI RF coil compared to a conventional RF array or coil or an iPRES coil or an oPRES array. There is also a need for a coil assembly that minimizes the number of RF chokes required in the shimming coil. More importantly, there is a need for a coil system that minimizes the interaction between the shimming coils and the RF coil array due to their mutual inductance, yet is still sufficiently flexible in design to meet imaging criteria for any part of a subject being imaged.

SUMMARY

One example is a Magnetic Resonance Imaging (MRI) system that includes a mechanical coil supporting structure and a coil array system. The coil array system includes an RF coil array having a plurality of coil elements. Each of the coil elements are operative in an RF mode for at least one of transmit or receive. A separate shim coil array has a plurality of coil elements operative in a direct current (DC) mode with DC current flow in the respective coil elements generating local B0 magnetic fields for B0 shimming. The two separate RF and shim coil arrays share the same surface or layer of the mechanical coil supporting structure, or reside in two separate mechanical coil supporting structures that are close each other.

The two separate RF and shim coil arrays are RF decoupled from each other by integrating blocking elements, such as RF chokes, in the shim coil arrays to minimize the RF interactions between two coil systems. Importantly, this decoupling is between an RF coil array (e.g., an antenna) and a shim coil array, which is a DC (direct current) device. A magnet bore of a MRI scanner holds a target object. The mechanical structure supports the separate RF coil and shim arrays to be positioned about the target object. A DC power supply is in communication with the shim coil array to supply DC current to the respective coil elements of the shim coil array. A shim coil circuit is in communication with the shim coil array configured to direct the DC power supply to supply the DC current to the respective coil elements to generate the local B0 magnetic fields for at least one of B0 shimming, MRI spatial encoding of spins, or MRI temporal encoding of spins. An RF circuit is in communication with the separate RF coil array configured to receive an MR signal from the object for RF receive or transmit RF pulses to the object for RF transmit.

Another example is a method of shimming Magnetic Resonance (MR) systems. At least one shim coil array with a plurality of coil elements is provided. The coil elements have associated circuits with a direct current (DC) current path comprising at least one loop. The at least one RF coil array is operated in at least one of an RF transmit or receive mode. The RF coil array is separate from the at least one shim coil array. The two separate RF and shim coil arrays share the same surface or layer of the mechanical coil supporting structure. The two separate RF and shim coil arrays are RF decoupled from each other by integrating blocking elements, such as RF chokes, in the shim coil arrays to minimize the RF interactions between two coil systems. DC current is flowed through the DC current paths of the coil elements of at least one shim coil array concurrently with the transmit or receive mode of at least one RF coil array. Local B0 magnetic fields are generated in response to the flow of the DC current through the DC current paths of the coil elements, thereby B0 shimming an imaging space of a magnet of the MR system using the generated local B0 magnetic fields.

Additional aspects of the invention will be apparent to those of ordinary skill in the art in view of the detailed description of various embodiments, which is made with reference to the drawings, a brief description of which is provided below.

BRIEF DESCRIPTION OF FIGURES

Exemplary embodiments are illustrated in referenced figures. It is intended that the embodiments and figures disclosed herein are to be considered illustrative rather than restrictive.

DETAILED DESCRIPTION

Figure 1:
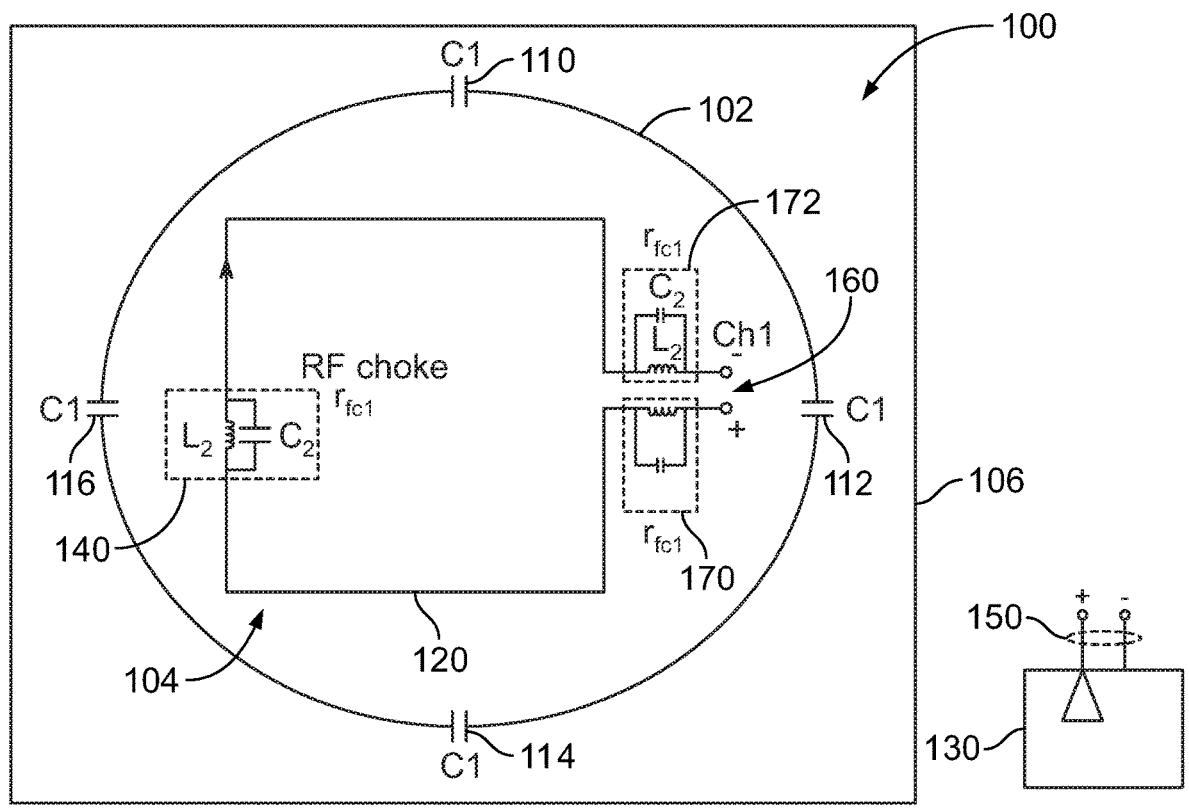
FIG. 1 is a circuit diagram of an example element design of a coil assembly with a separated RF coil and a shimming coil array.

FIG. 1 is a block diagram of a coil assembly 100 that includes a RF coil 102 and a shim coil 104 for a magnetic resonance system. The RF coil 102 is an outer circular shaped loop that represents a traditional RF-only loop coil. In a previous system, the loop coil by definition either receives MR radiofrequency (RF) signals as a receive-only RF coil from the spins in tissue or non-tissue material, or transmits RF pulses as a transmit-only RF coil to excite the spins in tissue or non-tissue material, or performs both functions as a transmit and receive RF coil. The coil 102 includes a number of distributed capacitors 110, 112, 114, and 116 that stabilize the performance of the coil 102. The number of capacitors such as the capacitors 110, 112, 114, and 116 is n, a positive integer. In this example, n=4. In this example and other examples in this specification, a traditional RF-only loop coil will follow the same definition, unless otherwise specified. The RF coil 102 and the shim coil 104 can be mounted on a coil supporting structure 106. The coil mechanical supporting structure 106 may be a coil helmet, coil housing, or any other mechanical coil assembly.

In this example, the diameter of the loop of the RF coil 102 may be between 1 cm and 100 cm depending on the application. For example, a cardiac coil array may include 16 loops, each being 10-20 cm in diameter, on a top chest structure and 16 loops, each being 10-20 cm in diameter, on a Bottom chest structure. A head coil may have 32 loops, each having a diameter of 5-12 cm. Of course other sized loops and number of loops may be used for different types of arrays. The typical frequency for the RF signal may be 63.9 MHz or 63.6 MHz for a 1.5 T scanner, 128 MHz or 123.2 MHz for a 3 T scanner, and 298 MHz for a 7 T scanner.

The shim coil 104 includes a square-shaped shim loop 120 that represents an example of the completely separate shim coil 104 in relation to the RF coil 102. Both the RF coil 102 and the shim loop 120 are a conductor material. The shim coil 104 in FIG. 1 is an example of a one channel shim coil with the DC current controlled by a controller 130. In this example, the controller 130 is a DC current source that includes source amplifiers that provides a DC current supply. As noted above, shim coil includes a square shim loop 120.

In the various embodiments, shim loops, such as shim loop 120, can be configured to include integrated blocking elements to block high frequency signal coupling into the shim loops. For example, high frequency signals generated by a nearby RF loop, such as RF coil 102. The blocking elements can be any type of circuit elements that block the propagation of a high frequency currents along the shim loops while allowing the propagation of lower frequency currents of direct current. In the various configurations described below, the blocking elements are embodied as RF chokes inserted along a shim loop, but this is solely for ease of illustration. It is contemplated that any other types of circuits with an equivalent function can be integrated into the shim loops. Moreover, it is contemplated that any inherent inductance or capacitance of the shim loops can be leveraged to completely or partially define the blocking elements.

The shim loop 120 can have n distributed RF chokes where n may be 0 or a positive integer. In this example, shim loop 120 has an RF choke 140 in the form of an inductor ($L_2$) in parallel with a capacitor ($C_2$). However, in the various implementations, any combination of inductors and/or capacitors and/or diodes may be used. The RF choke 140 prevents RF currents but allows DC currents in shim loop 120.

In the various configurations, the blocking elements can be configured in a variety of ways to prevent RF currents. In some configurations, a shim loop can be configured so that the resonant frequency of the blocking elements is at approximately the Larmor frequency for the MRI system. For example, the capacitor and inductor values in RF choke 140 can be selected so that the resonant frequency of the RF choke 140 is at the Larmor frequency of the MRI system, +/−15%. In other configurations, the inductance sufficiently high and acts to effectively block all but direct currents.

As shown above, shim coil 104 is associated with a channel that is controlled by the controller 130. The channel Ch1+− in FIG. 1 represent the positive and negative polarities of DC current feeding terminals 150 DC current source supply of the controller 130. The DC current for the shim coil 104 is independently controlled via a channel current amplifier in the controller 130 and provided to the shim coil 104 using a pair of DC feed wires 160. One or more RF chokes such as the RF chokes 170 and 172 can be inserted in the DC feed wires 160 to eliminate unwanted RF currents here as well. As shown in FIG. 1, the RF chokes 170 and 172 are each a parallel combination of an inductor and a capacitor in this example. However, in the various implementations, any other types of circuits for preventing RF currents but allowing DC currents can be used. The pair of DC feeding wires 160 can also be twisted together to avoid generating unwanted additional local magnetic fields.

The example of FIG. 1 is provided merely to illustrate a basic implementation, of a coil assembly according to the present disclosure, for ease of understanding. That is, one RF coil and one shim coil. However, the present disclosure contemplates a variety of modifications that can be applied to the example of FIG. 1.

In some implementations, the shim coils can be configured with any number of blocking elements. For example, referring back to FIG. 1, instead of the three RF chokes (140, 170, and 172), the blocking of unwanted RF currents can be provided using a single RF choke. Further in some cases, the shim loops can be designed to have a sufficient inherent inductance and/or capacitance, eliminating the need for a RF choke to be added. Additionally, these inherent properties of the shim coil can, in some cases, be tuned using additional elements. Thus, a shim coil may include zero or any positive integer of RF chokes configured as blocking elements.

In some implementations, a coil assembly can include multiple RF loops (e.g., up to 512) which together can form a traditional RF phased array coil. For at least one of RF loops, there can be at least one separate shim loop (e.g., 1-100) used. These shim loops can be placed anywhere nearby the RF loops, underneath, above, or at the same surface with the corresponding RF loop, overlapped or partially overlapped with RF loops and other shim loops.

In some implementations, for each shim loop with its 2 DC current feeding wires, the number of RF chokes in the shim loop and DC wires can vary (e.g., 0 to 1000). Further, the RF chokes can be placed anywhere in the shim loop and DC wires. In practice, the RF chokes should be arranged to avoid creating unwanted resonant spectrum modes close to the MR system Larmor frequency.

In some implementations, the shape of the RF and shim coils can vary. For example, a shape of each shim loop and the RF loop can be square, circular, rectangular, diamond, triangular, or any other shapes. Moreover, as shown in FIG. 1, the shapes need not be identical for all elements in a same coil assembly. Moreover, a size of identical shim loops can also vary (i.e., be larger or smaller).

In some implementations, the arrangement of shim loops can vary. That is, a relative position between separate shim loops in a shim array and the RF loop can be flexible. For example, one half of the shim array can be outside the RF loop while the other half can be inside the RF loop.

In some implementations, the shim coil and the RF coil are physically separate. The shim coil and the RF coil should not be in direct electrical contact. For example, any electrically conductive features defining the shim coil and the RF coil should not touch. In some implementations, such features can cross each other to minimize space and distance, but should be electrically insulated to prevent any electrical contact.

In some implementations, the shim loop can include constant and/or time varying DC currents. By varying the DC currents in the shim loop, the shim loop can generate time-varying B0 magnetic fields, which can be either used for dynamic B0 shimming to homogenize the magnetic field within region of interest (ROI) or for MRI spatial and/or temporal encoding of spins. Such methods can be used to enhance the differentiation of tissues at different locations by spatially and temporally manipulating B0 magnetic field, or it does both at the same time.

Figure 2:
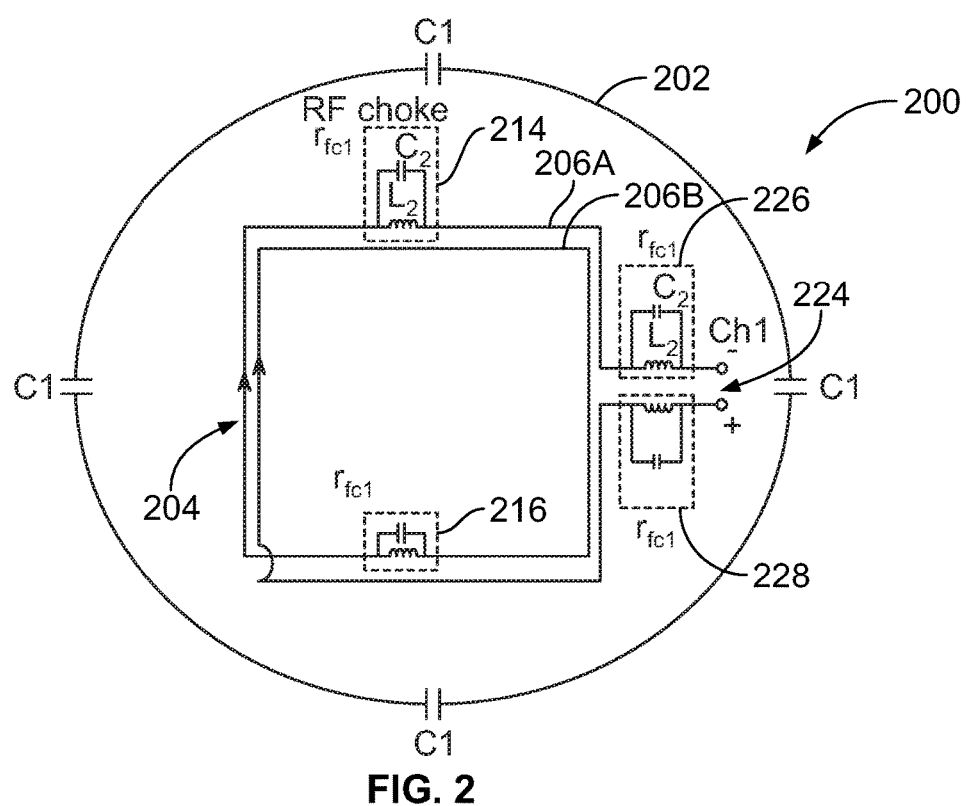
FIG. 2 is a circuit diagram of an example element design of a coil assembly with a separated RF coil and a shimming coil array with a two turn shim coil.

FIG. 2 shows a coil assembly 200 including a two-loop shim coil. The coil assembly 200 includes an RF coil 202. The circular shaped loop of the RF coil 202 represents a traditional RF-only loop coil. The coil assembly 200 includes a shim coil 204 with two rectangular shim loops 206A and 206B. The two shim loops 206A and 206B include respective RF chokes 214 and 216. A pair of DC current wires 224 each include an RF choke and provides current to the shim coil 204. The number of RF chokes for each of the pair of DC wires 224 and the shim loops 206A and 206B may be zero or any positive integer.

Similar to the coil assembly 100 of FIG. 1, the outer circular shape loop of RF coil 202 in FIG. 2 represents a traditional RF-only loop coil. The inner one square shape shim loops 206A and 206B represent one example of a completely 'separate' shim coil loop having 2-turns, which only work at direct current (DC) mode (i.e., zero or low frequencies less than 100 KHz).

FIG. 2 further shows shim coil 204 as 1-channel shim coil loop with the DC current in the shim loop independently controlled by a 1-channel DC current sources or supply. Compared to FIG. 1 (1 shim loop), the two shim loops 206A and 206B in FIG. 2 can provide a doubled shim magnetic field strength for the same DC current amplitude.

Although FIG. 2 shows only two RF chokes (214, 216), other implementations are possible. For example, a two square shim loop design can have n distributed RF chokes, where n can be 0 or a positive integer.

Similar to FIG. 1, Ch1+− in FIG. 2 represents the positive and negative polarities of DC current feeding terminals of a 1-channel DC current source. Note that the DC current for the shim coil 204 in FIG. 2 would be independently controlled by one channel of DC current amplifier/source. Also similar to FIG. 1, One or more RF chokes can be are inserted in the DC feed wires 224 to eliminate unwanted RF currents. For example, FIG. 2 shows RF chokes 226 and 228 being used in each of the pair of DC feed wires 224. The pair of DC feed wires 224 can be twisted together to avoid generating unwanted additional local magnetic fields and minimizes interaction with the RF coil 202 or any other RF loops present. Note the arrows here mean the DC shim current flow direction and it can be either positive (clockwise) or negative currents (counter-clockwise).

As with the example of FIG. 1, in the example of FIG. 2, any number of RF chokes can be used in the shim loops 206A and 206B and the DC feeding wires 224 to eliminate the unwanted RF currents potentially induced by the RF coil 202 (or other RF loops). Therefore, minimized interaction between shim loops and RF loops is achieved to minimize the signal to noise ratio (SNR) loss compared to the case having RF loop alone.

The same modifications and variations discuss above with respect to FIG. 1 can also be applied to the coil assembly of FIG. 2.

Figure 3:
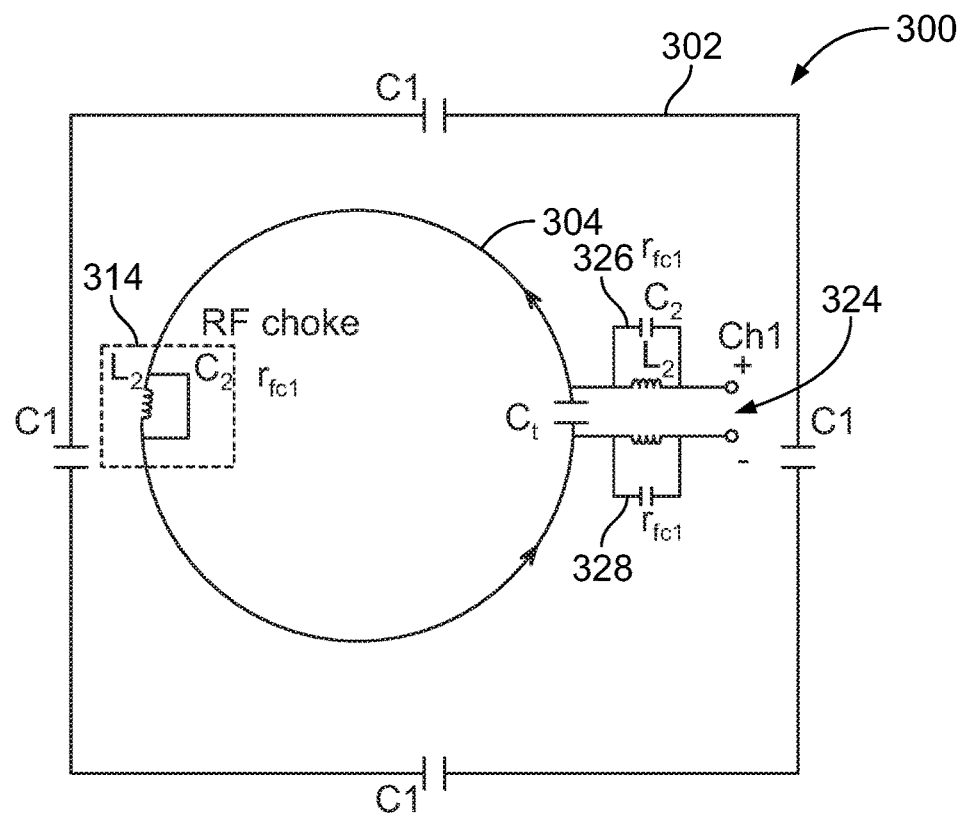
FIG. 3 is a circuit diagram of an example element design of a coil assembly with a separated RF coil and a shimming coil array using transformer decoupling for decoupling between shim and RF loops.

FIG. 3 shows a coil assembly 300 implementing transformer decoupling. The coil assembly 300 includes an RF coil 302 and a circular shim coil 304. A pair of DC current wires 324 each include an RF choke and provides current to the shim coil 304. The number of RF chokes for each of the pair of DC wires 324 and the shim coil 304 may be zero or any positive integer.

Similar to the coil assembly 100 of FIG. 1, the outer rectangular shape loop of RF coil 302 in FIG. 3 represents a traditional RF-only loop coil. The inner circular shaped shim coil 304 represents one example of a completely 'separate' shim coil loop.

FIG. 3 further shows shim coil 304 as 1-channel shim coil loop with the DC current in the shim loop independently controlled by a 1-channel DC current sources or supply.

Although FIG. 3 shows only one RF choke (314), other implementations are possible. For example, a circular shim coil design can have n distributed RF chokes, where n can be 0 or a positive integer.

Similar to FIG. 1, Ch1+− in FIG. 3 represents the positive and negative polarities of DC current feeding terminals of a 1-channel DC current source. Note that the DC current for the shim coil 304 in FIG. 3 would be independently controlled by one channel of DC current amplifier/source. Also similar to FIG. 1, One or more RF chokes can be are inserted in the DC feed wires 324 to eliminate unwanted RF currents. For example, FIG. 3 shows RF chokes 326 and 328 being used in each of the pair of DC feed wires 324. The pair of DC feed wires 324 can be twisted together to avoid generating unwanted additional local magnetic fields and minimizes interaction with the RF coil 302 or any other RF loops present. Note the arrows here mean the DC shim current flow direction and it can be either positive (clockwise) or negative currents (counter-clockwise).

As with the example of FIG. 1, in the example of FIG. 3, any number of RF chokes can be used in the shim coil 304 and the DC feeding wires 324 to eliminate the unwanted RF currents potentially induced by the RF coil 302 (or other RF loops). Therefore, minimized interaction between the shim coil and RF loops is achieved to minimize the signal to noise ratio (SNR) loss compared to the case having RF loop alone.

As shown in FIG. 3, a capacitor $C_t$ is applied, which is the transformer decouple capacitor. The value of capacitor $C_t$ can be chosen to be small, e.g., less than 1 pf, in order to create a high impedance in the shim coil 304 at the MR system Larmor frequencies. This in turn provides, better RF decoupling between the shim coil 304 and any RF loops present. Similarly, the transformer decoupling capacitor Ct can also be used in the case in FIG. 2 or any other configuration utilizing a shim coil with multiple shim loops.

The same modifications and variations discuss above with respect to FIG. 1 can also be applied to the coil assembly of FIG. 3.

Figure 4A:
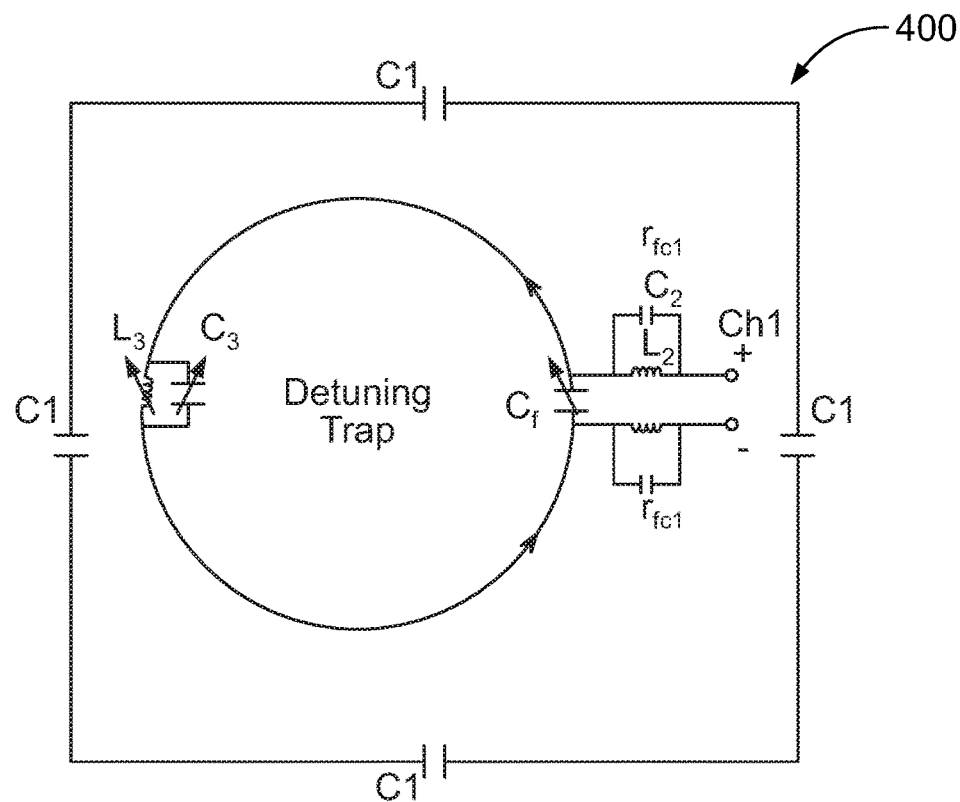
FIGS. 4A and 4B are circuit diagrams of an example element designs of a coil assembly with a separated RF coil and a shimming coil array using local detuning traps for decoupling between shim and RF loops.
Figure 4B:
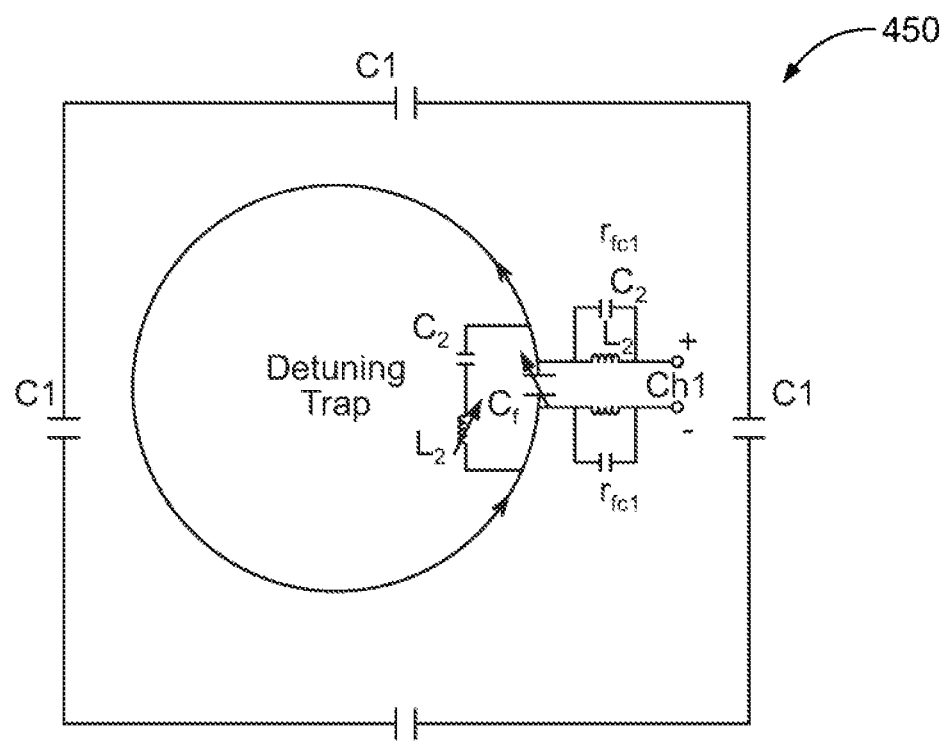

FIGS. 4A and 4B are other examples of separate shim loop designs, but using a local detuning-trap circuit. For ease of illustration, the coil assemblies 400 and 450 in FIGS. 4A and 4B, respectively, are configured substantially similar to coil assembly 300. That is, each of coil assemblies 400 and 450 has an outer square shape loop defining an RF coil and an inner circular loop defining a separate shim coil. The details of the components and descriptions are the similar to those described in FIGS. 1-3.

In the designs of FIGS. 4A and 4B, a detuning trap is used. In particular, a tuning frequency capacitor $C_f$ is provided that that tunes the shim coil to the MR system Larmor frequency. In the design of FIG. 4A, an adjustable L-C circuit (defined by the combination of adjustable inductor $L_3$ and adjustable capacitor $C_3$) is provided in series with tuning frequency capacitor $C_f$. The components of the L-C circuit can be adjusted to make the L-C circuit resonate at the Larmor frequency such that for the shim coil, the frequency response will have peaks at split frequencies. One peak is above the Larmor frequency and another peak is below the Larmor frequency. Further, there will be a large dip at the Larmor frequency (relative to the peak frequencies. Consequently, the shim loop becomes strongly decoupled from an RF loop resonating at the Larmor frequency. This is similar to detuning circuits used in traditional RF-receive coils where the detuned circuit is enabled by forwarding the bias current through a diode during RF transmit pulses. However, the difference here is that the detuning traps are only used in the shim coil for at least one of B0 shimming, MRI spatial encoding of spins, or MRI temporal encoding of spins.

In the design of FIG. 3B, the adjustable L-C circuit is provided in parallel with tuning frequency capacitor $C_f$. Thus, the detuning circuit comprises L2, C2, and Cf. Other detuning circuit designs can be used in other implements. Further, detuning traps can also be used for shim coils with multiple shim loops, such as that shown in FIG. 2.

The same modifications and variations discussed above with respect to FIG. 1 can also be applied to the coil assemblies of FIGS. 4A and 4B.

Although the coil assemblies of FIGS. 1, 2, 3, 4A, and 4B consist of a shim coil associated with a single control channel, the present disclosure contemplates using the design methods disclosed for providing shim coils for use with multiple channels. This is illustrated in FIGS. 5 and 6.

Figure 5:
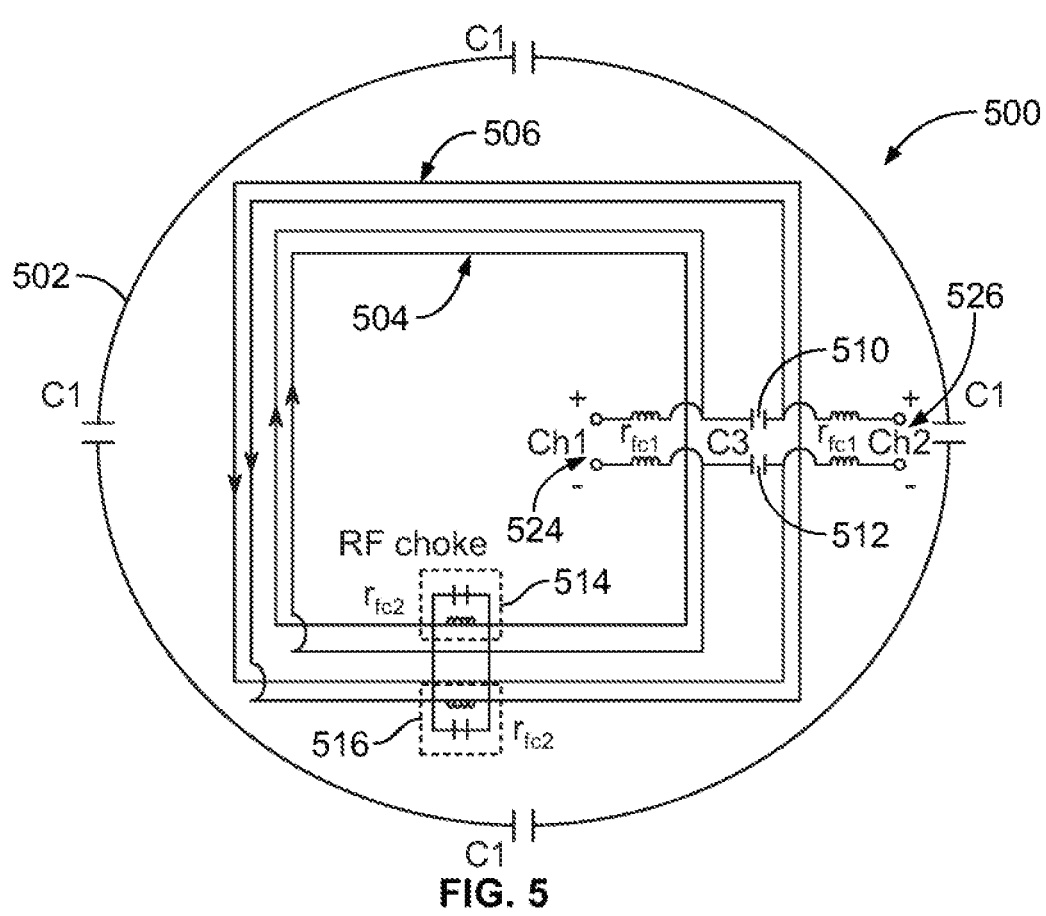
FIGS. 5 and 6 are different alternatives of an example element design of a coil assembly with an RF coil separated from a shimming coil array.
Figure 6:
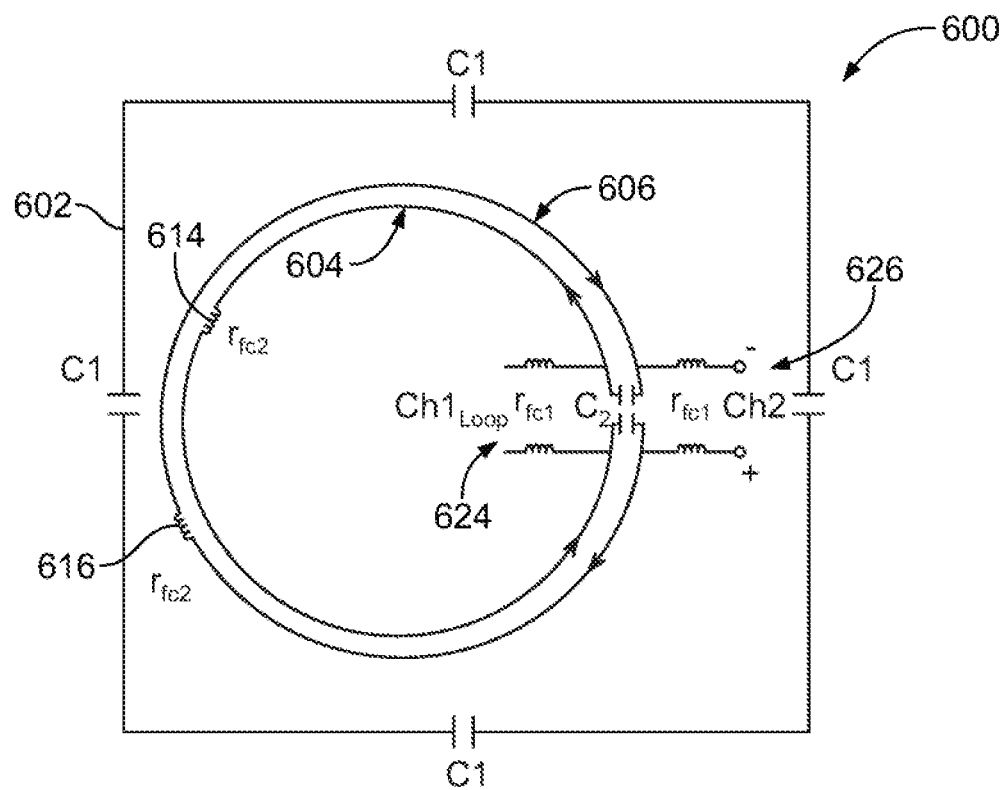

FIG. 5 shows a coil assembly 500 that is one example of a shim coil array for use with two control channels. FIG. 6 shows another coil assembly 600 that is another example of a two-loop shim coil array. In both coil assemblies 500 and 600, the shim coils represent a two-channel shim coil that is controlled by a current controller with two channels.

Turning first to FIG. 5, the coil assembly 500 includes an RF coil 502. The circular shaped loop of the RF coil 502 represents a traditional RF-only loop coil. The coil assembly 500 also includes two inner rectangular shim coils 504 and 506. Each of these shim coils is similar to the shim coil in FIG. 2. That is each of shim coils 504 and 506 include multiple turns. In FIG. 5, the two shim coils 504 and 506 are connected through a pair of DC blocking capacitors 510 and 512 that may be between 0-10,000 PF. The shim coils 504 and 506 include respective RF chokes 514 and 516. A pair of DC current wires 524 and 526 each includes an RF choke and provides current to the respective shim coils 504 and 506. The number of RF chokes for each DC wire and shim coil may be any positive integer. In the example of FIG. 5, the shim coils 504 and 506 are arranged concentrically relative to the RF coil 502. However, other arrangements can be provided. For example, the shim coils 504 and 506 can be arranged next to each other or in an overlapping manner.

In coil assembly 500, undesirable RF currents (potentially induced by the RF coil 502) will flow in shim coils 504 and 506 along the paths directed by the arrows. Note the arrows here mean the direction of RF currents potential induced by the RF coil 502. In this example, shim coil 504 has the counter-clockwise direction of RF currents which flow to shim coil 506 through one pair of capacitors $C_2$. As such, shim coil 506 has a clockwise direction of RF currents with the same amplitude as that in shim coil 504. Since the RF currents are the same, magnetic fluxes generated by the potential RF currents in the shim coils 504 and 506 cancel each other. Thus, the mutual inductance between the shim coils 504 and 506 and the RF coil 502 is zero and the shim coils 504 and 506 are thus inherently decoupled from the RF coil 502.

As exemplified by FIGS. 2 and 5, all the shim coil configurations set forth in this disclosure may be extended to multiple turns or loops, such as two, three, or more. The multiple turns allow for decreased currents to produce the same shim fields as a single turn loop. Alternatively, the multiple turns allow for the same current level to produce a multiplied shim field strength compared to a single turn coil. By enabling multi-turn/loop shim coils, the shim field strength can be multiplied to meet the challenges presented by ultra-high (7T or greater) static magnetic fields. With these ultra-high magnetic fields, high shim strengths are necessary, and can also reduce shim current amplitudes to minimize heat dissipation.

Similar to coil assembly 500 in FIG. 5, the coil assembly 600 in FIG. 6 includes an RF coil 602 and a two-channel shim array including a shim coil 604 and a shim coil 606. The two shim coils 604 and 606 are circular and arranged concentrically with respect to each other and RF coil 602. The shim coils 604 and 606 include respective RF chokes 614 and 616. A pair of DC current wires 624 and 626 each includes an RF choke and provides current to the respective shim coils 604 and 606. The number of RF chokes for each DC wire and shim coil may be zero or any positive integer.

The two shim coils 604 and 606 are connected through a pair of DC block capacitors and each includes RF chokes ($r_{fc2}$). Similar to the coil assembly 500, undesirable RF currents induced by the RF-only coil 602 flow along the path directed by the arrows. The magnetic flux generated by RF currents have opposite signs in the two identical shim coil 604 and 606 and cancel each other. The mutual inductance between the two channel shim array of the shim coil 604 and 606 and the RF coil 602 is zero and the shim array is thus inherently decoupled from the RF coil 602.

In FIGS. 5 and 6, Ch1+−, and Ch2+− represent the positive and negative polarities of DC current feeding terminals of a 2-channel DC current source supply. The DC current for each shim channel is independently controlled by a separate channel current amplifier. As shown in FIGS. 5 and 6, one or more RF chokes ($r_{fc1}$) can inserted in the DC feed wires to eliminate unwanted RF currents. However, as noted above, no RF choke needs to be inserted if the inherent capacitance and/or inductance of the shim coils provides the necessary blocking capabilities.

Further, the shim coil configurations set forth in this disclosure can be used to form a shim coil array. In such configurations, the number of the shim coils comprising an array alike can be any positive integer.

Advantageously, in the various configurations according to the present disclosure, shim coils need not be arranged in a geometrical symmetry in relation to the respective RF loop coil, in contrast to WO 2017/079487. That is, there is no need that the shim coils be connected and routed sequentially in a way that unwanted RF currents induced by the RF loop coil generate magnetic flux of opposite polarities in each adjacent pair of two shim coil loops. Rather, shim coils according to the present disclosure can be arranged in any needed arrangement since blocking of unwanted RF currents is handled by the blocking elements associated with the shim coils.

In the various configurations according to the present disclose, the size of identical shim loops in a shim coil array may be larger or smaller than the RF loop. Also, the relative positions between the separate shim coil array and RF loop can be flexible as long as the RF chokes are properly configured to zero or minimize the mutual inductance between two coil systems. For example, one half of the shim coil array can be outside the RF loop while the other half can be inside the RF loop but both coil systems can be still completely decoupled.

Further, the shim coil array and RF-only coil are physically completely separate. In some configurations, these coils can share the same surface of a coil support structure. Alternatively, these coils can reside in two separate mechanical coil supporting structures that are close to each other. The wires comprising the shim array and the wires comprising the RF coil can cross each other with minimal distance but use insulated wires without electrical contact.

The coil assemblies described above, allow for the expansion of more shim loops than the number of available RF receivers resulting in increased shimming performance because of greater number of shimming loops. The resulting assemblies when used in an MRI system may greatly increase image fidelity and resolution, for example in fMRI of important brain regions prefrontal cortex and temporal cortex and in cardiac imaging of heart/lung Boundaries.

The assemblies described may be generally applied to coils for imaging all parts of a human or animal body, such as, for example, head coils, head neck spine coils, cardiac coils, body coils, torso coils, breast coils, musculoskeletal coils, knee coils, foot/ankle coils, carotid coils, wrist coils, and Cervical/Thoracic/Lumbar coils. The assemblies may also be applied to imaging non-tissue material including petroleum rock core, food, chemical system, and any other materials. The assemblies may be generally applied to all human or animal MRI scanners or even MR spectrometers and can be generally applied to any main magnetic B0 field strengths, 1.5 T, 3 T, and 7 T. The assemblies may be applied to any MRI system equipped by any number of RF receivers.

The minimal requirement for the modification of MRI hardware architecture will make an easy transfer to next generation scanners. The add-on ability compared to a traditional RF array allows for upgrades as it does not require increase of radial or longitudinal dimensions of RF arrays and will look similar to a traditional coil and be used like a traditional coil after integrating the coil to the scanner.

The RF array may be a traditional RF coil/array, a receive-only coil/array, or a transmit-only coil/array, or a Transmit/Receive coil/array. It can be of any design, gapped or partially overlapped designs, or any other designs. The total number of RF receiver channels or DC shim channels in a unified coil system can be any positive integer, i.e., 1-4, 8, 16, 24, 32, 48, 64, 96, 128, 192, 256, and etc.

As noted above, the shapes of each element shim loop and the RF loop can be any closed curve, any polygon, square, circular, rectangular, diamond, triangular, or any other shapes, and their sizes and positions can be flexible.

In any of the implementations disclosed herein, the distance between the RF coil array and the shim coil array is generally minimized. Because of the presence of the RF blocking elements in shim coil array/shim loop elements, the shim coils can be placed in close proximity to the RF coil array without the mutual inductance between the two interfering with the operation of the system. Thus, by decoupling the RF coil array and the shim coil array with the RF blocking element, the mutual inductance is minimized. In some implementations, the distance between the RF coil array and the shim coil array is approximately 0.0 millimeters, such that at least a portion of the RF coil array physically contacts at least a portion of the shim coil array. In other implementations, the distance between the RF coil array and the shim coil array can be between about 0.0 millimeters and about 5.0 millimeters, between about 0.0 millimeters and about 10.0 millimeters, between about 0.0 millimeters and about 20.0 millimeters, between about 5.0 millimeters and about 10.0 millimeters, between about 50.0 millimeters and about 100.0 millimeters, between about 0.0 millimeters and about 100.0 millimeters, or between about 5.0 millimeters and about 100.0 millimeters. This can be accomplished with minimal or zero RF sensitivity loss due to the presence of the RF blocking elements.

Figure 7:
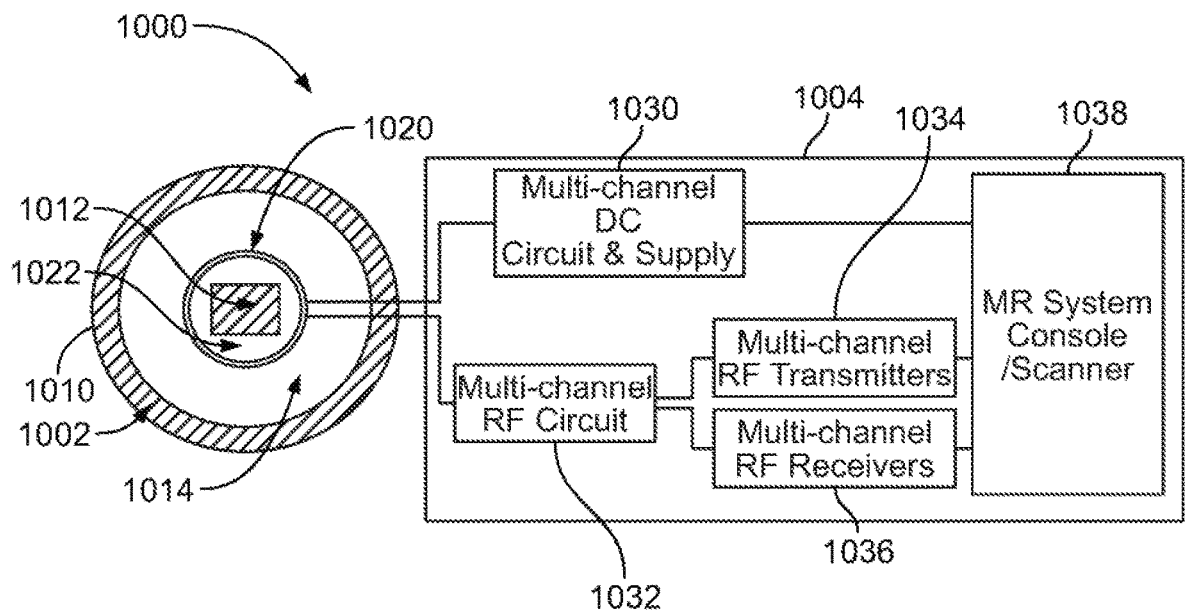
FIG. 7 is a block diagram of an MRI system that incorporates coil assemblies with separated RF and shim coil arrays.

FIG. 7 is an example of the Magnetic Resonance Imaging (MRI) system 1000. The system 1000 includes an MRI scanner 1002 that is controlled by an MRI control system 1004. In this example, MRI scanner 1002 includes a tubular supporting structure 1010 that surrounds a target object 1012 that may be a patient. The tubular supporting structure 1010 forms a bore 1014 that includes a permanent or superconducting (high-field magnet) that generates a static magnetic field (B0) of large magnitude such as 1.5 T, 3 T or 7 T. The target object 1012 is in proximity to a coil array system 1020 that is supported by a mechanical coil supporting structure 1020. The control system 1004 includes scanner operating components such as RF amplifiers, gradient amplifiers, controllers, and processors that typically direct the pulse sequences and select the scan planes of the target object 1012.

The unified coil array system 1020 may be composed of any of the coil assemblies described above such as the coil assemblies where the RF coil and shim coil arrays are separated, such as in FIGS. 1-6 or any variations thereof. Thus, the coil array system 1020 may include an RF coil array having a plurality of coil elements where each of the coil elements are operative in an RF transmit mode or RF receive mode. The coil array system 1020 also includes a shim coil array having a plurality of coil elements operative in a direct current (DC) mode with DC current flow in the respective coil elements to generate local $B_0$ magnetic fields for $B_0$ shimming. In FIG. 7, the RF coil array and the shim coil array are geometrically overlapped and share the same surface or layer of the supporting structure 1022. However, this is only for ease of illustration. Rather, any arrangement of the RF coil array and the shim coil array can be used. As noted above, the RF coil array and the shim coil array are decoupled by decoupling methods as above described with respect to FIGS. 1-6 (or any variations thereof) to minimize the RF interaction between two coil systems.

The MRI control system 1004 includes a multi-channel DC circuit and current supply 1030, a multi-channel RF control circuit 1032, a multi-channel RF transmitter 1034, a multi-channel RF receiver 1036, and a control console 1038. As explained above, the DC circuit and current supply controller 1030 is in communication with the shim coil array of the united coil array system 1020 to supply DC current to the respective coil elements of the shim coil array. The DC controller 1030 includes a shim coil circuit that is in communication with the shim coil array configured to direct the DC power supply to supply DC current to the respective coil elements to generate the local $B_0$ magnetic fields for $B_0$ shimming. The DC controller 1030 allows separate control of each shim coil via separate channels.

The multi-channel RF control circuit 1032 is in communication with the RF coil array of the united coil array system 1020. The RF control circuit 1032 is configured to receive an MR signal from the target object 1012 via the multi-channel RF receiver 1036. The RF control circuit 1032 is also configured to transmit RF pulses to the target object 1012 from the multi-channel RF transmitter 1036.

The control console 1038 controls the multi-channel DC circuit and current supply 1030, the multi-channel RF control circuit 1032, the multi-channel RF transmitter 1034, the multi-channel RF receiver 1036 to transmit RF signals, adjust the shimming and receive RF signals in conjunction with the scanning function. Generally, the RF circuit controller 1032 is in communication with the MRI scanner 1002 to cause the RF coil array of the unified coil array system 1020 to transmit and receive while causing the shim coil array to perform at least one of B0 shimming an imaging space, MRI spatial encoding of tissue spins, or MRI temporal encoding of tissue spins using the generated local $B_0$ magnetic fields from the shim coil array. The multiple shimming coils allow the controller 1030 to be configured to generate the local $B_0$ magnetic fields to provide a uniform magnetic field across the target object 1012. This creates better imaging from the MRI scanner 1002. Other functions associated with the scanning process may also be performed. For example, the console 1038 may control shim coil circuit of the DC controller 1030 to generate $B_0$ maps associated with the generated local $B_0$ magnetic fields and perform B0 shimming. The console 1038 may also control DC current in the coil elements of the shim coil array via the DC controller 1030 and measure the generated local $B_0$ magnetic fields.

Figure 8:
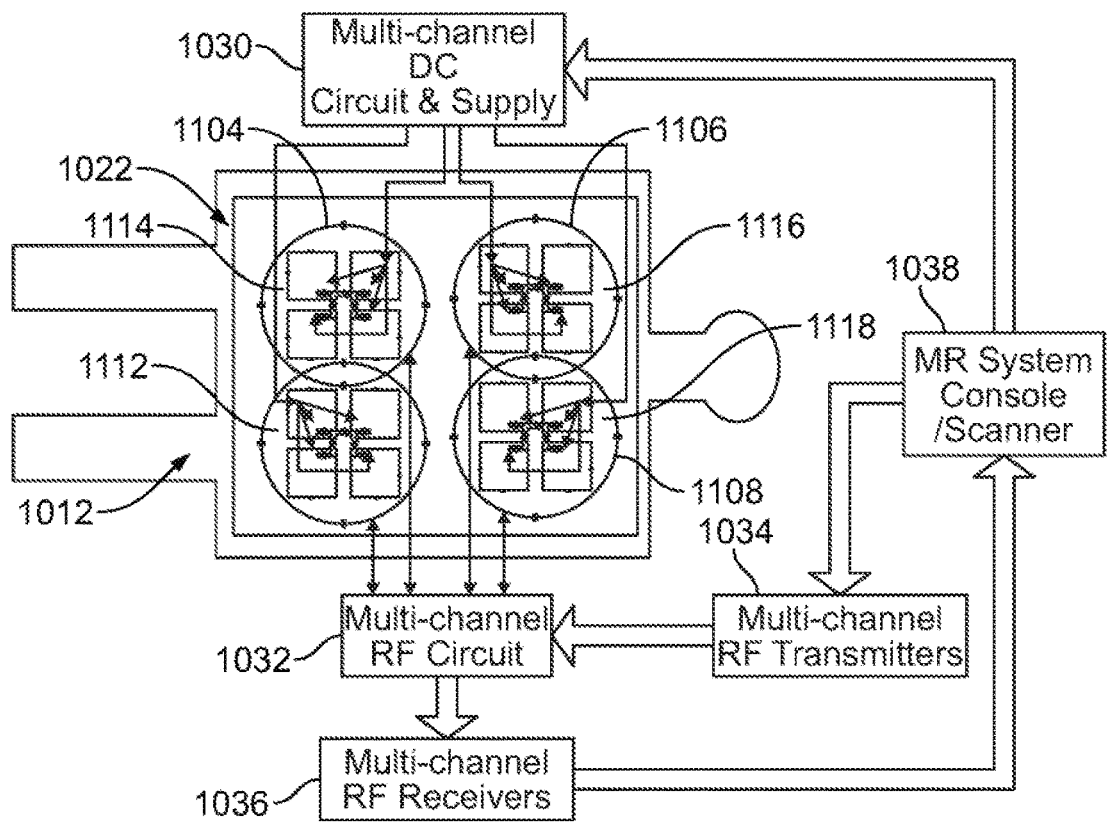
FIG. 8 is a block diagram of a unified coil array that has separate RF and shim coil arrays used in the MRI system in FIG. 10.

FIG. 8 shows a block diagram of the use of coil assemblies such as those shown in any of the previous examples as part of the unified coil array system 1020. In FIG. 8, like elements are labeled with like numbers as in FIG. 7. As shown in FIG. 8, the coil support structure 1020 allows placement of an RF coil array having four coil elements 1102, 1104, 1106, and 1108 in proximity to the target object 1012. As explained above, the RF coil elements 1102, 1104, 1106, and 1108 are coupled to the multi-channel RF circuit 1032 for receive and transmit modes. Each of the RF coil elements 1102, 1104, 1106, and 1108 are physically separated from shim coil arrays 1112, 1114, 1116, and 1118. The shim coil arrays 1112, 1114, 116, and 1118 are controlled for shimming by the DC controller 1030. In FIG. 8, the separate RF coil array and shim coil arrays 1112, 1114, 1116, and 1118 are geometrically overlapped and share the same surface or layer of the mechanical coil supporting structure 1022. Again, as with FIG. 7, this arrangement is presented only for ease of illustration. As noted above, the various configurations allow for any arrangement of RF coil arrays relative to shim coil arrays.

In this example, since there are four RF coil elements 1102, 1104, 1106, and 1108, the RF control circuit is a four-channel circuit. The shim coils are controlled via a multiple channel DC controller such as the DC controller 1030. Of course more or less RF coils may be used and more or less shim coils may be used with corresponding control channels.

Although the foregoing description has been primarily focused on the use of RF chokes as the blocking elements, the RF chokes throughout the above described examples may alternatively be an RF trap or filter using at least one inductor and at least one capacitor in parallel connection. Such traps or filters would also be set to have a resonant frequency adjusted and matched to the Larmor frequency of the MRI system. A low frequency AC power supply to supply a low frequency AC current may be used instead of the DC power supply for the shim coil arrays in the above examples.

The above examples may be applied to almost all MR coil systems including musculoskeletal coils with less receive channels (1-8), birdcage coils and even animal scanners, to meet various challenges in fMRI, DTI, MRSI and etc., and greatly improve image quality in air/tissue/Bone interfaces from head to toe. Alternatively, the shim coils of the above examples may be replaced with gradient coils each having at least one coil element operative in a direct current (DC) or low frequency alternating current (AC) mode for spatial encoding of the spins to be imaged.

The above described systems are based on decoupling methods as in FIGS. 1-6 (or any variations thereof) that dramatically reduces RF interaction to almost negligible levels so that maximal S is maintained and RF chokes are reduced to one per DC loop, advantageous for 7T MRI applications. Multiple turns largely increase shim field strengths for deep tissues shimming and 7T MRI systems, where higher shim field strengths are necessary.

Figure 9:
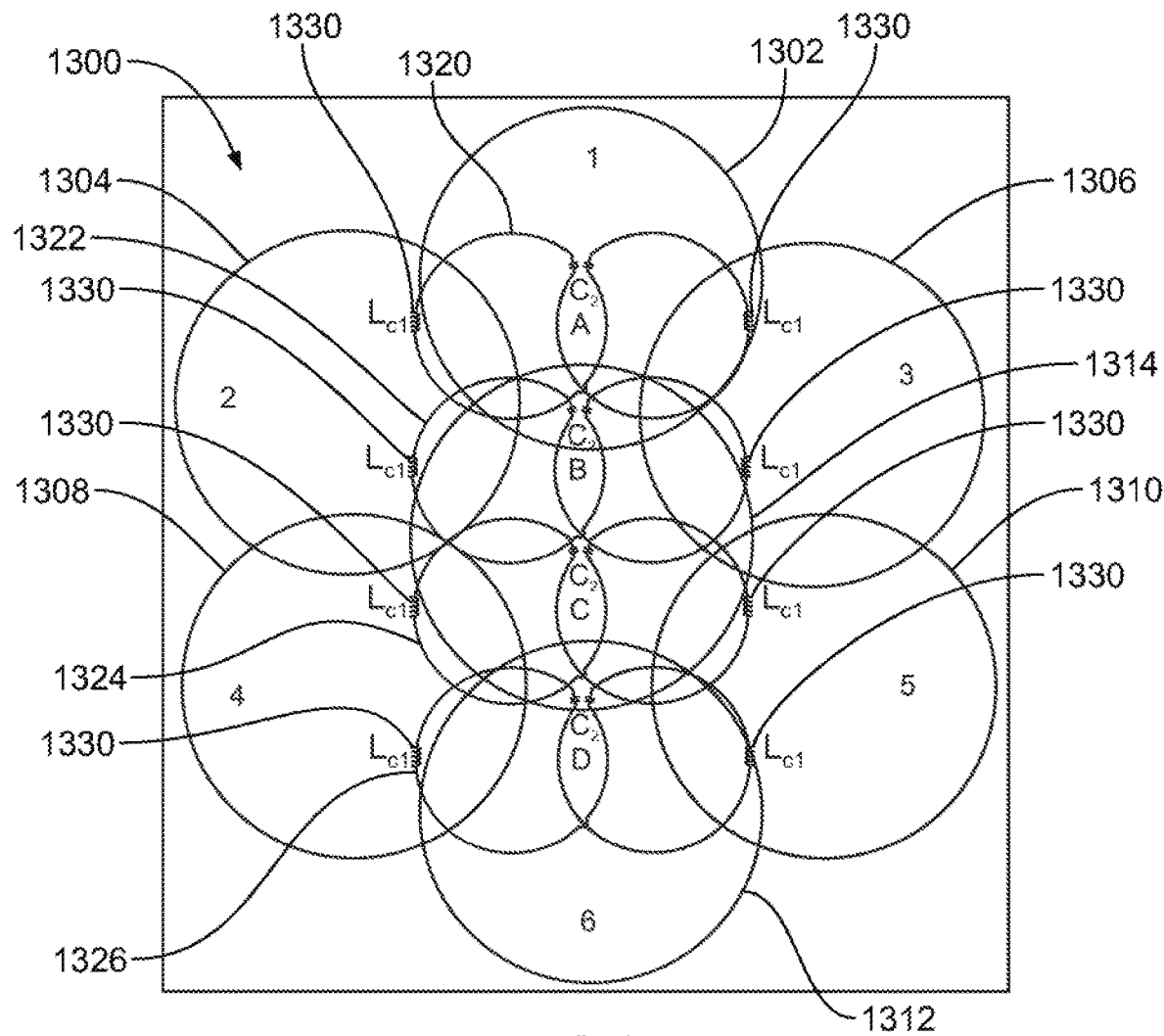
FIG. 9 is a circuit diagram of an example U C array for brain imaging.

FIG. 9 shows an example array 1300 for brain imaging. The array 1300 includes seven large diameter loops 1302, 1304, 1306, 1308, 1310, 1312, and 1314 for RF reception. The loops 1302, 1304, 1306, 1308, 1310, and 1312 are RF/DC shared-conductor loops (iPRES designed loops according to the description in WO 2014/003918 A1, hereby incorporated by reference. The loop 1314 is an RF-only loop. The array 1300 includes four shim loops 1320, 1322, 1324, and 1326 that are separate shim loops targeting shimming of prefrontal cortex (PFC) or temporal lobes (TLs). The shim loops 1320, 1322, 1324, and 1326 (loops A B C and D) are decoupled from both the RF-only loop 1314 and the RF/DC shared loops 1302, 1304, 1306, 1308, 1310, and 1312. This is done using blocking elements (e.g., RF chokes) as describe above.

In FIG. 9, the shim loops 1320, 1322, 1324, and 1326 are illustrated as figure-8 loops, but no specific geometry is required for the loops 1320, 1322, 1324, and 1326. Rather, any of the shim coil arrangements described above with respect to FIGS. 1-6 (or any variations thereof) can be used.

Figure 10:
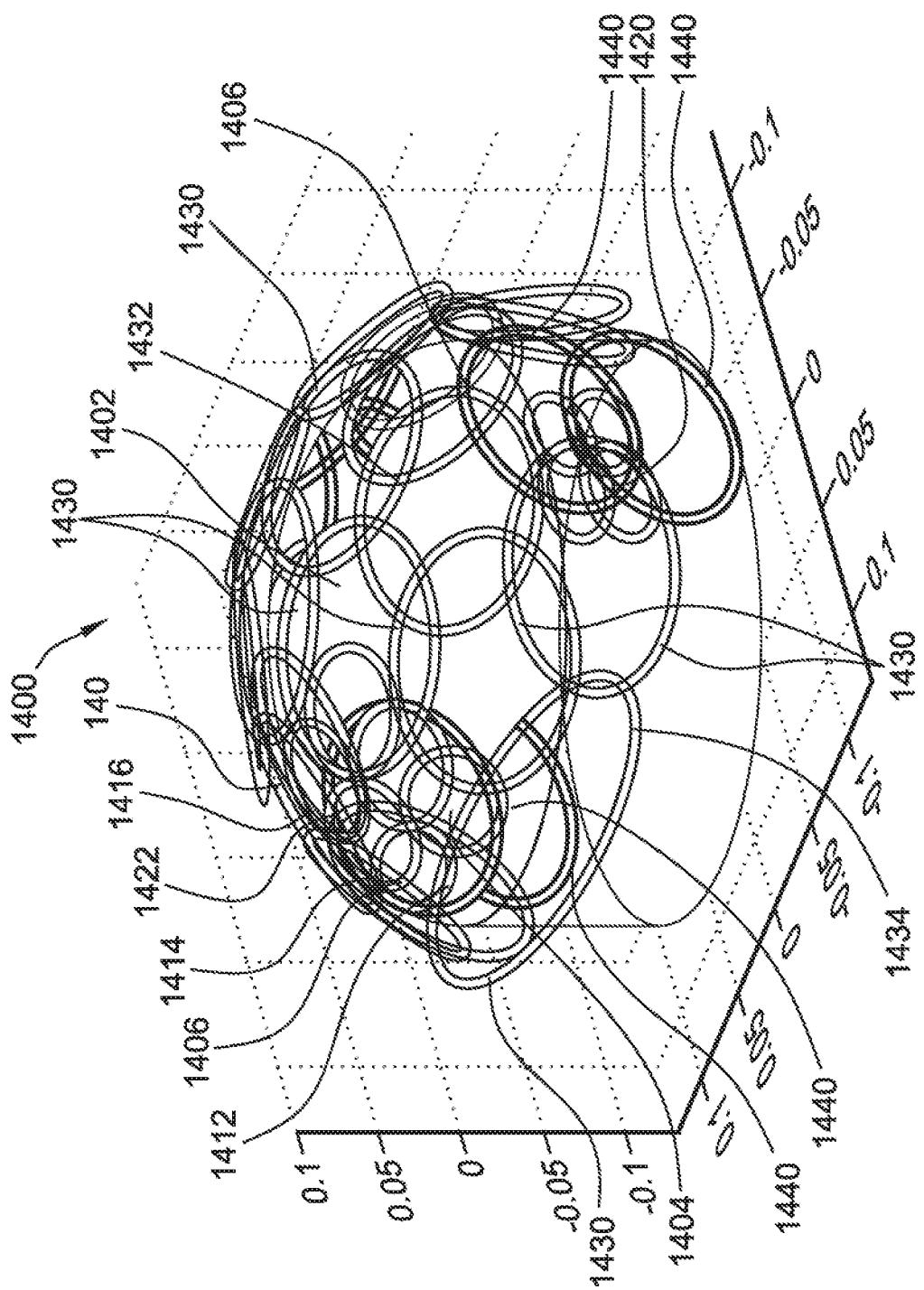
FIG. 10 is a head coil for brain imaging using the circuit in FIG. 9.

A whole head array is shown in FIG. 10, where sizes of the shim loops match those of anatomical structures. In addition, separate shim loops can enable multiple-turn, overcoming another major limit in shim field strength as iPRES loops are limited to a single turn only.

Alternatively, the RF-only loop 1314 can also be an iPRES RF/DC loop or RF-only loops. The four pairs of shim-only loops 1320, 1322, 1324, and 1326 consist of eight independently controlled DC loops for B0 shimming. The DC feeding wires and current source supplies are not shown for simplicity of illustration in FIG. 10.

A practical example of using the array 1300 may be a brain fMRI coil. In such an application, four pairs of figure-8 shim-only loops may be placed as close as possible to the prefrontal cortex and each temporal lobe. The size may be matched to be 4-6 cm diameter of each circular DC loop for the PFC and 3-5 cm diameter of each circular DC loop for the temporal lobes. The nested large RF loops may be up to 32 channels for a scanner equipped by 32 channel RF receivers. The RF loops can be either RF-only loop such as the RF-only loop 1314 or an RF/DC iPRES type loop such as the loop 1302. The complexity is actually reduced because each DC loop only requires fewer RF chokes (0, 1, or n) while each iPRES loop requires 2-6 chokes. More importantly the shim-only loops effectively target the PFC and temporal lobe shimming.

While FIG. 10 utilizes figure-8 shim-only loops, this is only for convenience and ease of illustration. The shim-only loops in FIG. 10 can be replaced by any of the shim loop configurations illustrated in FIGS. 1-6 or any variations thereof.

The concepts of the brain application for the array in FIG. 10 may be generally applied to other coils for imaging other parts of human or animal body. To that end, the shape of the shim loops can be selected to be advantageous for the particular part of the body being imaged. Further, the number of shim loops may be any integral number above 1. Additionally, the size of the loops 1302, 1304, 1306, 1308, 1310, 1312 and 1314 may be any range of sizes. Finally, single or multiple turn shim loops can be used as well.

FIG. 10 shows a head coil design 1400 for brain imaging under construction with 31-channel RF reception and 48-channel shimming. The coil design array 1400 is used for scanning a brain 1402 that includes a prefrontal cortex 1404 and temporal lobes 1406 of interest. Sizes and shapes of shim loops are selected to match those of anatomical structures. In addition, separate shim loops may be multiple-turn, overcoming another major limit in shim field strength as iPRES loops are limited to one turn only.

The head array 1400 includes three separate DC shim loops 1412, 1414, and 1416 at the prefrontal cortex. In this example, figure-8 shaped DC shim loops that are 5 cm in diameter. Two groups of shim loops 1420 and 1422 are located at each temporal lobe 1404. The loops in the groups of shim loops 1420 and 1422 are 4 cm in diameter in this example. The head array 1400 includes a group of eight iPRES loops 1430, a group of seventeen iPRES loops 1432 and a single IPRES loop 1434 that are arranged around the brain 1402 that perform RF reception and B0 shimming simultaneously. In this example the loops 1430, 1432 are 9.5 cm in diameter. The example head array 1400 also includes five RF-only loops 1440 that are in proximity to the prefrontal cortex 1402 and temporal lobes 1404. In FIG. 10, the shim loops 1412, 1414, 1416, 1420 and 1422 are illustrated as figure-8 loops, but as noted above, no specific geometry is required for the loops 1412, 1414, 1416, 1420 and 1422. Rather, any of the shim coil arrangements described above can be used. The shim loops 1412, 1414, 1416, 1420 and 1422 can be alternatively any of the shim loops as illustrated in FIGS. 1-6.

The head array in FIG. 10 can target the prefrontal cortex, the temporal lobe, the spinal cord, or a metallic implant in the patient's head. Other implementations can have size-matched shim coil arrays for other targeted anatomical structures, not just the head. For example, a metallic implant anywhere in the body could be targeted using a size-matched shim coil array. Generally, any anatomical structure that presents results in an inhomogeneous B0 field can be targeted/imaged using a size-matched shim coil array. Any number of shim coil loops of any size can be placed as close as physically possible to the target anatomical structure (such as the mesial temporal lobe or orbitofrontal cortex) without causing patient discomfort and without losing RF sensitivity. Target anatomical structures can include, but are not limited to, a prefrontal cortex, a temporal lobe, a spinal cord, a metallic implant within the target object, a heart, a breast, an abdominal region, or any other fine anatomical structure in the target object.

As noted above, the decoupling in the various configurations is provided via the configuration of the RF chokes being incorporated. An RF choke is usually an inductor in parallel with a capacitor but can have different forms of circuit designs. It prevents RF currents but allows DC currents. The function of RF chokes is that the parallel LC circuit has a resonant frequency at or close to the MR system Larmor frequency, which creates a high impedance if inserted into loops or wires, to prevent RF currents on the loops or wires and to minimize RF interactions with the RF loop.

Figure 11:
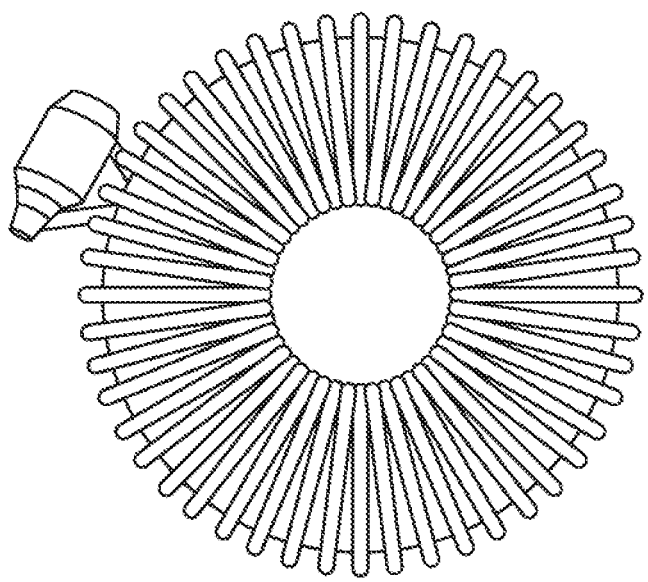
FIG. 11 is a photo of an exemplary RF choke.

Further, an RF choke can have different forms of designs: 1) An inductor in parallel with a capacitor. FIG. 11 shows a toroid inductor (~800 nH, 33 turns, size 1.9 cm) in parallel with a capacitor (1.2 pf). The toroid inductor is self-shielded to minimize its RF interactions with environments. The inductor can also be other forms, e.g., solenoidal, or other geometries. 2) The choke can be a large value inductor alone, e.g. over 800 nH. 3) It can be an inductor alone but the inductor has its own self-resonance frequency at or close to the MR system Larmor frequencies. 4) It can be any other electronic designs.

Figure 12:
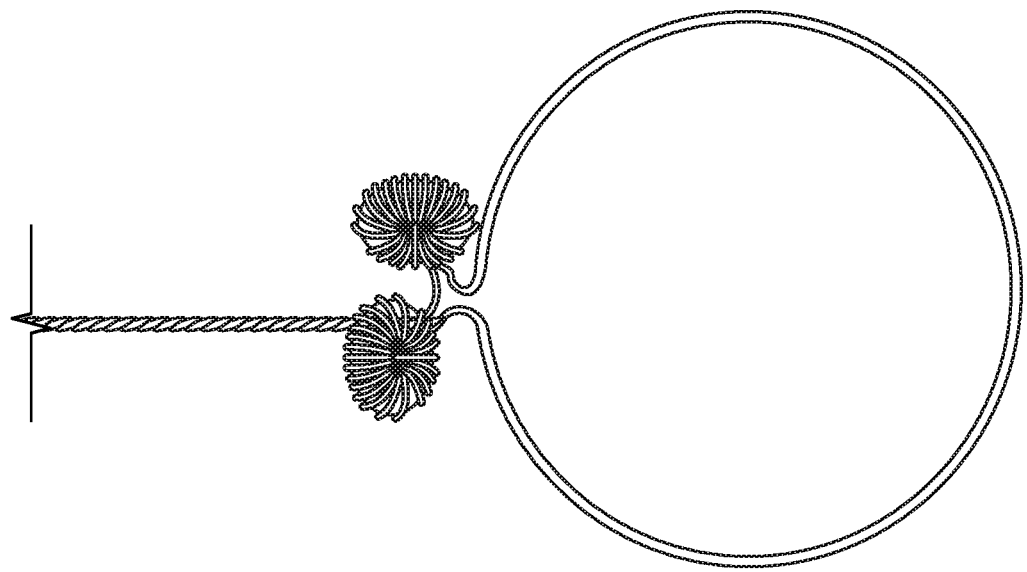
FIG. 12 is a photo of an exemplary single turn shim coil with RF chokes.

FIG. 12 is the photo of one shim loop design of FIG. 1. No chokes in the shim loop (7.5 cm diameter) Two chokes are shown in the pair of twisted DC wires, which are connected to one channel DC current amplifier.

Figure 13:
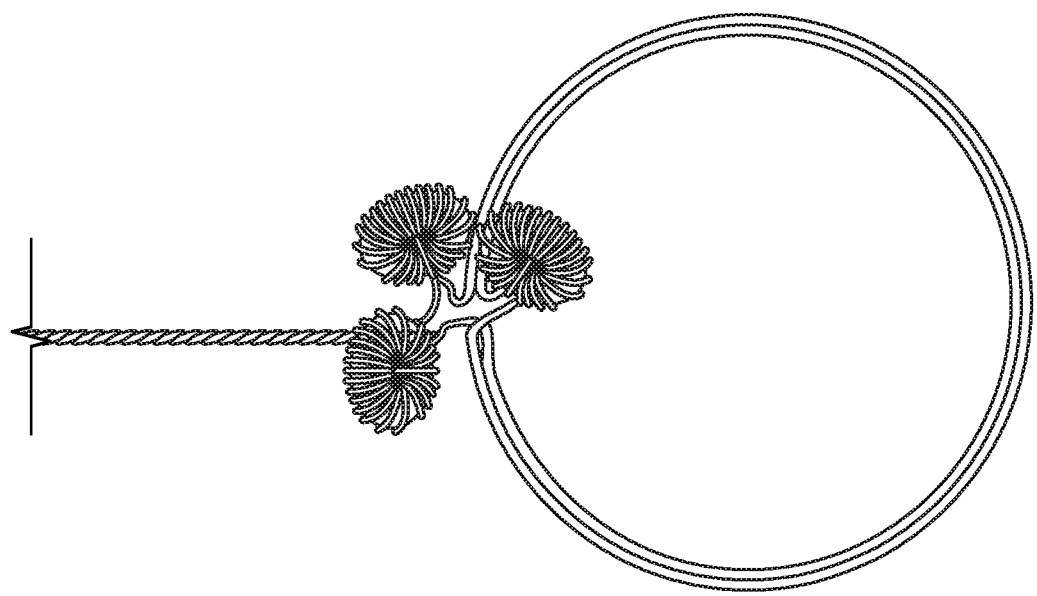
FIG. 13 is a photo of an exemplary two turn shim coil with RF chokes.

FIG. 13 is the photo of one shim loop design of FIG. 2. One choke is used in the 2-turn shim loop (7.5 cm diameter). Two chokes are shown in the pair of twisted DC wires, which are connected to one channel DC current amplifier.

The foregoing choke designs are provided merely by way of example and not by way of limitation. The present disclosure contemplates that other choke designs can be used in the various configuration according to the present disclosure. For example, a solenoid design can be used.

Because of the RF blocking elements in the shim coil array, the coupling (e.g. mutual inductance) between the RF coils and the shim coils is minimized and thus the distance between the RF coils and the shim coils can be zero. Thus, there can be physical contact between the RF coils and the shim coils without compromising the RF sensitivity of the RF coils, even if the RF coils have no RF shielding. This ensures that both the RF coils and the shim coils are placed as closed to the subject as possible, which maximizes the performance with regard to both RF sensitivity and shimming.

In any of the implementations disclosed herein, the system may include any number of RF coil elements. Each RF coil element can have N shim coil elements associated therewith, where N can a positive integer. Moreover, some of the RF coil elements do not have any shim coil elements associated therewith, such that N=0.

While various examples and configurations have been described above, it should be understood that they have been presented by way of example only, and not limitation. Numerous changes to the disclosed examples and configurations can be made in accordance with the disclosure herein without departing from the spirit or scope of the present disclosure. Thus, the breadth and scope of the present disclosure should not be limited by any of the above disclosed examples and configurations. Rather, the scope of the present disclosure should be defined in accordance with the following claims and their equivalents.

Although the scope of the present disclosure has been illustrated and described with respect to one or more implementations, equivalent alterations and modifications will occur to others skilled in the art upon the reading and understanding of this specification and the annexed drawings. In addition, while a particular feature may have been disclosed with respect to only one of several implementations, such feature may be combined with one or more other features of the other implementations as may be desired and advantageous for any given or particular application.

The terminology used herein is for the purpose of describing the examples and configurations herein only and is not intended to be limiting of the present disclosure. As used herein, the singular forms "a", "an" and "the" are intended to include the plural forms as well, unless the context clearly indicates other-wise. Furthermore, to the extent that the terms "including", "includes", "having", "has", "with", or variants thereof are used in either the detailed description and/or the claims, such terms are in-tended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense un-less expressly so defined herein.

What is claimed is:

1. A Magnetic Resonance Imaging (MRI) system, comprising:
   a coil array system including:
      an RF coil element operative in an RF mode for at least one of transmit or receive; and
      a separate shim coil array having one or more shim coil elements operative in a direct current (DC) mode with DC current flow in the shim coil elements generating local B0 magnetic fields for at least one of B0 shimming, MRI spatial encoding, or MRI temporal encoding;
      wherein at least part of the RF coil element and separate shim coil array overlap each other, and wherein the separate shim coil array includes at least one RF blocking element for decoupling the separate shim coil array from the RF coil element;
   a magnet bore of a MRI scanner holding a target object, the RF coil element and separate shim coil array positioned about the target object;
   a DC power supply in communication with the shim coil array to supply DC current to the shim coil elements of the shim coil array;
   a shim coil circuit in communication with the shim coil array configured to direct the DC power supply to supply the DC current to the shim coil elements; and
   an RF circuit in communication with the RF coil element configured to receive an MR signal from the object for RF receive or transmit RF pulses to the object for RF transmit.

2. The system of claim 1, wherein the RF coil element is one of a plurality of RF coil elements in an RF coil array, and wherein N of the shim coil elements are associated with one of the plurality of RF coil elements in the RF coil array, the RF coil array being a receive-only RF coil array, a transmit-only RF coil array, or a transmit/receive RF coil array.

3. The system of claim 2, wherein the separate shim coil array comprises at least one pair of DC wires, and wherein at least one of the pair of DC wires includes an RF blocking element.

4. The system of claim 3, wherein the RF blocking element in the at least one of the pair of DC wires is configured to pass at least one of direct current or a current with a frequency of 1 MHz or less.

5. The system of claim 3, further comprising at least one capacitor coupling the at least one of the pair of DC wires, the at least one capacitor having a capacitance of less than 100 pF.

6. The system of claim 1, wherein the RF blocking element comprises a circuit having a resonant frequency that is between about 85% of a Larmor frequency of the MRI system and about 115% of the Larmor frequency of the MRI system.

7. The system of claim 6, wherein the circuit comprises at least one of an inductor and a capacitor.

8. The system of claim 6, wherein the circuit comprises an inductor with an inductance greater than 100 nH.

9. The system of claim 1, wherein at least one of the shim coil elements a multiple-turn loop.

10. The system of claim 2, wherein one of the respective N shim coil elements comprises a detuning trap configured to cause a frequency response of the shim loop to be split around the Larmor frequency of the MR system.

11. The system of claim 2, wherein at least two of the N shim coil elements are sequentially connected though a pair of DC blocking capacitors.

12. The system of claim 2, wherein the DC power source includes N channel circuits controlled by the shim circuit, each of the N channel circuits corresponding to one of the N shim coil elements, and wherein the shim circuit allows individual adjustment of a DC current in each of the N shim coil elements.

13. The system of claim 1, wherein the shape of the shim coil element, the RF coil element, or both, is one of a closed curve, a polygon, a circular shape, a square shape, a rectangular shape, a diamond shape, or a triangular shape.

14. The system of claim 2, wherein the coil array system includes a plurality of closely stacked layers of individually operable discrete RF coil elements of the RF coil array and the separate shim coil array.

15. The system of claim 1, wherein a distance between the RF coil element and the separate shim coil array is approximately zero such that least a portion of the RF coil element and at least a portion of the separate shim coil array are physically touching.

16. The system of claim 1, wherein the distance between the RF coil element and the separate shim coil array is between about 0 millimeters and about 10 millimeters.

17. The system of claim 1, wherein the RF coil element and the separate shim coil array are positioned in an identical mechanical holding structure of the system.

18. The system of claim 1, wherein the RF coil element is decoupled from the separate shim coil array such that a mutual inductance between the separate shim coil array and the RF coil element is minimized.

19. The system of claim 1, wherein a size of one or more shim loop elements in the separate shim coil array are matched to a size of a target anatomical structure of the target object, the target anatomical structure having an inhomogeneous field, and being a prefrontal cortex, a temporal lobe, a spinal cord, a metallic implant within the target object, a heart, a breast, an abdominal region, or any other fine anatomical structure in the target object.

20. The system of claim 19, wherein the separate shim coil array includes one or more shim coil elements, and wherein a distance between each of the one or more shim coil elements and the target anatomical structure of the target object is minimized.

21. The system of claim 1, wherein the at least one RF blocking element includes an inductor with an inductance of at least 800 nH.

22. The system of claim 1, wherein the one or more shim coil elements includes a first set of one or more shim coil elements and a second set of one or more shim coil elements that is sequentially connected to the first set of one or more shim coil elements though a pair of DC blocking capacitors, the second set of one or more shim coil elements being positioned concentrically inside of the first set of one or more shim coil elements.

23. The system of claim 22, wherein the first set of one or more shim coil elements includes a first circular shim coil element having one or more turns, and wherein the second set of one or more shim coil elements includes a second circular shim coil element having one or more turns, the second circular shim coil element being positioned concentrically inside of the first circular shim coil element.

24. The system of claim 22 wherein the first set of one or more shim coil elements includes a first rectangular shim coil element having one or more turns, and wherein the second set of one or more shim coil elements includes a second rectangular shim coil element having one or more turns, the second rectangular shim coil element being positioned concentrically inside of the first rectangular shim coil element.

25. The system of claim 1, wherein the shim coil array includes a transformer decouple capacitor formed in-line with the at least one shim coil element, the transformer decouple capacitor being configured to generate a high impedance in the shim coil array at a Larmor frequency of the MRI system.

26. The system of claim 1, wherein the one or more shim coil elements of the shim coil array are arranged in geometrical asymmetry relative to the RF coil element.

27. The system of claim 1, wherein the one or more shim coil elements includes a single shim coil element.

28. The system of claim 1, wherein each of the one or more shim coil elements have an inherent inductance sufficient to decouple the separate shim coil array from the RF coil element.

* * * * *